United States Patent [19]
Heidlas et al.

[11] Patent Number: 5,811,563
[45] Date of Patent: Sep. 22, 1998

[54] PROCESS FOR THE FRACTIONATION OF WOOL WAX ACID MIXTURES

[75] Inventors: Jürgen Heidlas, Trostberg; Martin Ober, Altenmarkt; Jan Cully, Garching, all of Germany

[73] Assignee: SKW Trotestberg AK, Germany

[21] Appl. No.: 614,131

[22] Filed: Mar. 12, 1996

[30] Foreign Application Priority Data

Mar. 17, 1995 [DE] Germany .................. 195 09 760.2

[51] Int. Cl.$^6$ ..................................... C07C 1/00
[52] U.S. Cl. .............................. 554/11; 554/12; 554/20
[58] Field of Search .................... 584/11, 12, 20

[56] References Cited

U.S. PATENT DOCUMENTS 5,290,959  3/1994  Rice .......................................... 554/11

FOREIGN PATENT DOCUMENTS 0088405  9/1984  European Pat. Off. .
294280  9/1991  Germany .
1360460  7/1974  United Kingdom .

*Primary Examiner*—Gary Geist
*Assistant Examiner*—Deborah D. Carr
*Attorney, Agent, or Firm*—Felfe & Lync

[57] ABSTRACT

Disclosed is a process for the fractionation of wool wax acid mixtures by dissolving the starting material in a polar organic solvent (mixture). The dissolved wool wax acid mixture is treated at a temperature between -5 and 30° C. and at a pressure between 10 and 70 bar with gaseous carbon dioxide and the hydroxy-fatty acids that accumulate as a solid are separated from the solution.

12 Claims, No Drawings

PROCESS FOR THE FRACTIONATION OF WOOL WAX ACID MIXTURES

BACKGROUND OF THE INVENTION

The present invention concerns a process for the fractionation of wool wax acid mixtures that enables the fraction of hydroxy-fatty acids to be separated from the fraction of non-hyroxylated fatty acids and thus enables the hydroxy-fatty acids to be obtained as a crystalline product and in high purity.

A chemically nonhomogenous fraction of long chain carboxylic acids can be obtained from natural wool wax (lanolin) which are essentially composed of branched and unbranched fatty acids as well as hydroxy-fatty acids and above all alpha-hydroxy-fatty acids (Motiuk, K.; J. Am. Oil Soc. 56, 91 (1979)). The interest in suitable processes to separate the complex mixture of acids has arisen since the cosmetic and pharmaceutical industries have discovered their different use in various fields of application. A particular advantage in this connection is the toxicological safety of wool wax and its components in particular for topical applications in cosmetic formulas (J. Environ. Path. Tox. 4, 63–92 (1980)).

In the corresponding literature numerous procedures are described which can be used to separate mixtures of wool wax acid. These processes are based on the techniques of distillation, crystallization or solvent extraction, but all of these processes have considerable disadvantages. In distillation processes there is a general tendency that the potential product is prone to undesired reactions by an excessive thermal stress such as e.g. lactide formation between two alpha hydroxy acid molecules or dehydration reactions which ultimately cause high losses in yield.

In crystallization processes solvent mixtures have often been used for which relatively long crystallization procedures have to be employed providing poor space-time yields and consequently, less advantageous process economy. Additionally, these processes generally lead to an inadequate separation. Recently a new solvent process for the fractionation of wool wax acid mixtures was disclosed in EP 0 555 776 A1 which recommends at least two extraction steps with organic solvents of different polarity in order to obtain a effective separation and adequate purity of the acid fractions. In order to achieve a high product purity the process cycle of crystallization may have to be repeated several times with an additional salting-out procedure. Apart from the long processing time, which is in the range of several hours, a major technological problem may occur when carrying out the process on a large scale: the undissolved fatty acid fractions are often wax-like and/or of highly viscous consistency and tend to block the filter system. The objective of that process, which is to obtain the hydroxy-fatty acids in a pure and crystalline form, can only be achieved in a very complicated manner and with technological problems.

The object of the present invention is therefore to present a process for the fractionation of wool wax acid mixtures that circumvents the said disadvantages of the known processes in order to achieve a straightforward fractionation of the starting materials into hydroxylated and non-hydroxylated fatty acid fractions of high purity.

THE INVENTION

The above stated object is achieved according to the invention by dissolving the mixture of wool wax acids in a polar solvent (mixture), subjecting this solution to a pressure treatment with gaseous carbon dioxide at temperatures between −5 and 30° C. and at a process pressure between 10 and 70 bar and precipitating by this way the hydroxy-fatty acids as a solid from the solution. Surprisingly it has been found that the expansion behaviour of the respective solvent can be specifically controlled by the pressure of the gaseous carbon dioxide effecting a selective precipitation of the hydroxy-fatty acids in crystalline form that can be recovered from the solution in a straightforward manner.

According to the invention polar organic solvents with up to 5 C atoms from the series of short-chained esters such as in particular ethyl acetate, ketones such as in particular acetone and alcohols such as methanol and ethanol or mixtures of these solvents are used to dissolve the starting material. The mixture of wool wax acids to be fractionated is dissolved in these solvents preferably at a concentration between 10 and 50 % by weight, particularly preferably between 20 and 40 % by weight, and at room temperature i.e. preferable between 15 and 25° C. for which only a few minutes are required.

The fractionation procedure with this solution is subsequently carried out by subjecting the solvent (mixture) to a pressure of gaseous carbon dioxide at a temperature between −5 and 30° C. over a certain period of time, between 5 and 60 minutes. The dissolution of the gas in the solvent (mixture) causes an expansion of the volume of the solvent thus effecting the precipitation of the hydroxy-fatty acid fraction. It is expedient to carry out the process in a temperature-controlled pressure vessel. The maximum process pressure at a given temperature is limited by the pressure at which the carbon dioxide gas begins to liquefy which, however, is not quite reached in the fractionation according to the present process. At the maximum process temperature of 30° C. fractionating pressure attains its maximum value i.e. about 70 bar; at the minimum process temperature of −5° C. the pressure is about 25 bar. After a period of 5 to 60 minutes at fractionation conditions (pressure and temperature) which completes the precipitation, the obtained sediment, mainly composed of the hydroxy-fatty acid mixture, is separated from the solution while maintaining the process conditions constant. According to a preferred embodiment this separation step is carried out in a technically advantageous manner by means of a filter plate at the bottom of the pressure vessel in front of the outlet as filtering device to recover the precipitate. The non-hydroxylated fatty acids which essentially remain in solution can be isolated from the filtrate after the separation step, preferably by removing the organic solvent (mixture) by evaporation, optionally under reduced pressure.

The yield and purity of the precipitated hydroxy-fatty acids can be directed according to the invention by the process parameters, temperature and carbon dioxide pressure, and the selected solvent (mixture). Thus the separation of the mixture can be specifically controlled with these process parameters in accordance with the objective of the process.

In a further preferred embodiment of the process according to the invention the hydroxy-fatty acids, which accumulate as a crystalline precipitate are washed with liquid carbon dioxide. The washing effects the removal of the solvent residues and undesired flavor compounds and considerably improves the quality of the product. For this purpose the carbon dioxide is used at subcritical temperatures of <30° C. and at pressures of <100 bar i.e. in a liquid state. Due to the fact that the hydroxy-fatty acids have only a very low solubility in liquid carbon dioxide, the washing procedure can be performed without significant losses of product. The amount of liquid carbon dioxide for the washing step can be varied within a wide range depending on the degree of the desired improvement in quality. Advantageously, the amount for washing is selected between 0.5 and 100 g carbon dioxide per g hydroxy-fatty acid.

This rewashing of the filter residue with liquid carbon dioxide enhances the purity of the hydroxy-fatty acids by removing solvent residues leading to a dry product and effecting at the same time the elimination of the undesired characteristic odor of the starting material.

The significant advantages of the process according to the invention in comparison with the known processes are consequently that the hydroxy-fatty acids can be accumulated as a crystalline product which can be readily separated by filtration and that the process time can be kept comparatively short so that a good space/time yield can be achieved. Moreover, the process can be carried out under mild temperature conditions avoiding thermal damage to the products.

The following examples are intended to elucidate these advantages of the process according to the invention.

EXAMPLES

The process examples were carried out in a high pressure autoclave with an inspection glass and jacket cooling (autoclave volume 400 ml). A sintered metal plate is located at the bottom of the autoclave in front of an exit over which the sediment composed of hydroxy-fatty acids can be separated. The wool wax acid mixture (WWA) used has a hydroxy number of 60.

| Example | 1 | 2 | 3 |
| --- | --- | --- | --- |
| Solvent | Acetone | Ethyl acetate | Ethanol |
| Solvent volume (ml) | 50 | 50 | 50 |
| WWA in solution (% by weight) | 25 | 25 | 25 |
| $CO_2$ pressure (bar) | 30 | 28 | 30 |
| Temperature of the pressure treatment (°C.) | 0 | −5 | 0 |
| Time for sedimentation (min) | 45 | 45 | 30 |
| Relative sediment yield (% of WWA) | 21 | 17 | 18 |
| OH number of the filtrate residue | 190 | 182 | 210 |
| OH number of the eluate | 26 | 35 | 27 |
| Rehashing with $CO_2$ | — | — | + |
| Temperature (°C.) | — | — | 25 |
| Pressure (bar) | — | — | 75 |
| Amount of $CO_2$ for washing (g/g hydroxy-fatty acid mixture) | — | — | 3 |

It will be understood that the specification and examples are illustrative but not limitative of the present invention and that other embodiments within the spirit and scope of the inventions will suggest themselves to those skilled in the art.

We claim:

1. A process for the fractionation of wool wax acid mixtures comprising:

dissolving the starting material in a polar organic solvent;

treating the dissolved wool wax acid mixture with gaseous carbon dioxide at a temperature from −5 to 30° C. and at a pressure from 10 to 70 bars whereby a hydroxy-fatty acid fraction is produced as a solid; and, separating the hydroxy-fatty acid from the solution.

2. The process of claim 1, wherein the polar organic solvent is comprised of esters, ketones and alcohols with up to 5 C atoms and mixtures thereof.

3. The process of claim 1, wherein the polar organic solvent is selected from the group consisting of ethyl acetate, acetone, methanol, ethanol and mixtures thereof.

4. The process of claim 1, wherein the wool wax acid mixture is added to the polar organic solvent in a concentration range of 10 to 50% by weight.

5. The process of claim 4, wherein the concentration range is 20 to 40% by weight.

6. The process of claim 1, wherein the wool wax acid mixture is added to the polar organic solvent at a temperature of from 15 to 25° C.

7. The process of claim 1, wherein the hydroxy-fatty acid mixture is separated from the polar organic solvent by filtration.

8. The process of claim 1, further comprising washing the separated hydroxy-fatty acid mixture with liquid carbon dioxide.

9. The process of claim 8, wherein the rewashing with liquid carbon dioxide is carried out at a temperature <30° and a pressure <100 bar.

10. The process of claim 8, wherein the ratio of liquid carbon dioxide to the hydroxy-fatty acid mixture for the washing is (0.5 to 100):1.

11. The process of claim 1, wherein the process is conducted in a temperature-controlled pressure vessel with a filter plate which is located at the bottom in front of the vessel outlet.

12. The process of claim 7, wherein the wool wax acid mixture contains non-hydroxylated fatty acids and the non-hydroxylated fatty acids are isolated from the filtered solution by removing the solvent.

* * * * *